(12) United States Patent
Gow

(10) Patent No.: US 6,361,570 B1
(45) Date of Patent: Mar. 26, 2002

(54) UPPER LIMB PROSTHESIS

(75) Inventor: David James Gow, Edinburgh (GB)

(73) Assignee: Lothian Primary Care NHS Trust

( * ) Notice: Subject to any disclaimer, the term of this patent is extended or adjusted under 35 U.S.C. 154(b) by 0 days.

(21) Appl. No.: 09/530,175

(22) PCT Filed: Oct. 26, 1998

(86) PCT No.: PCT/GB98/03186

§ 371 Date: Apr. 24, 2000

§ 102(e) Date: Apr. 24, 2000

(87) PCT Pub. No.: WO99/21517

PCT Pub. Date: May 6, 1999

(30) Foreign Application Priority Data

Oct. 24, 1998 (GB) .............................................. 9722403

(51) Int. Cl.$^7$ ................................................. A61F 2/42
(52) U.S. Cl. ........................................... 623/62; 901/29
(58) Field of Search ............................. 623/58, 60, 62, 623/57, 61; 901/25, 28, 29

(56) References Cited

U.S. PATENT DOCUMENTS

| | | |
|---|---|---|
| 2,477,463 A | 7/1949 | Otterman |
| 2,482,555 A | 9/1949 | Otterman |
| 2,592,842 A | 4/1952 | Alderson |
| 4,114,464 A | 9/1978 | Schubert et al. |
| 4,955,918 A | 9/1990 | Lee |
| 5,413,454 A | 5/1995 | Movsesian .................. 414/729 |

FOREIGN PATENT DOCUMENTS

| | | |
|---|---|---|
| EP | 0 219 478 | 4/1987 |
| GB | 607 001 | 2/1947 |
| GB | 1 386 942 | 3/1975 |
| GB | 2 146 406 A | 4/1985 |
| GB | PCT/GB95/00518 | 9/1995 |

*Primary Examiner*—Bruce Snow
(74) *Attorney, Agent, or Firm*—Young & Basile

(57) ABSTRACT

The present invention provides an articular endoskeletal prosthesis 1 for providing a user with at least one of a mechanically operable pivoting wrist, elbow and shoulder joint. The prosthesis 1 has at least one elongate endoskeletal tube upper limb member 5 with a proximal end portion 6 having a pivotal connection 7 to a support body 9 therefor. One of said upper limb member proximal end portion 6 and said support body 9 has a fixed worm gear wheel means 19 and the other a drive motor 22 having a drive output worm 25 extending generally tangentially of said worm gear wheel means 19 for engagement with the gear teeth of said worm gear wheel means 19 so that when said drive motor 22 is operated, in use of the prosthesis 1, said upper limb member 5 moves around said worm gear wheel means 19 so as to pivot said upper limb member about its pivotal connection 7.

16 Claims, 1 Drawing Sheet

UPPER LIMB PROSTHESIS

FIELD OF THE INVENTION

The present invention relates to upper limb prostheses and in particular to such prostheses with mechanically (usually electro-mechanically) operable pivoting wrist, elbow and/or shoulder joints.

BACKGROUND OF THE INVENTION

The design of such prostheses presents various problems in relation to design flexibility and manufacturing cost, cosmetic appearance, power, stability etc. It will be appreciated that upper limb prostheses have relatively high power and strength requirements due to, inter alia, the considerable leverage forces exerted when, for example, using the prosthesis to lift objects more or less at arm's length. Thus previously known prostheses are essentially exoskeletal in nature with a relatively substantial large diameter shell structure shaped and finished to have the appearance of an upper limb or part thereof. With this type of construction it is necessary for a substantial part of the manufacture of the prosthesis to be customised to each individual patient, and in the case of children, to different developmental stages thereof. As the customised shell is also used as the main structural load bearing component and the support for the various operating mechanisms of the upper limb this results in relatively high costs and extended manufacturing processes. In addition, where, as is usually desirable, a rotating wrist is used, then the cosmetic appearance is compromised by the visibility of the join or discontinuity between the rotating and non-rotating parts of the prosthesis. In addition the motors used require relatively complex gearing systems and often the inclusion of secondary motors in order to provide the required power, and the necessary locking of the joint under load in a desired attitude, respectively. This in turn leads to increased weight, reduced design flexibility and relatively high power consumption.

SUMMARY OF THE INVENTION

It is an object of the present invention to avoid or minimise one or more of the above disadvantages.

It has now been found that by the use of a worm gear system for mechanically operating the prosthesis, the construction of upper limb prostheses can be very considerably simplified whilst maintaining performance comparable with or better than that of conventional externally powered upper limb prostheses.

In more detail the present invention provides an articular endoskeletal prosthesis for providing a user with at least one of a mechanically operable pivoting wrist, elbow and shoulder joint, said prosthesis having at least one elongate endoskeletal tube upper limb member with a proximal end portion having a pivotal connection to a support body therefor, one of said upper limb member proximal end portion and said support body having a fixed worm gear wheel means and the other a drive motor having a drive output worm extending generally tangentially of said worm gear wheel means for engagement with the gear teeth of said worm gear wheel means so that when said drive motor is operated, in use of the prosthesis, said upper limb member moves around said worm gear wheel means so as to pivot said upper limb member about its pivotal connection.

Thus with a prosthesis of the present invention construction may be greatly simplified by using more or less plain conventional lightweight tubing of relatively small diameter (as compared with the limb diameter) and which can readily be cut to any desired length. The relatively simple and compact form of drive mechanism also contributes to simplifying construction and reducing the strength and size requirements of the tubing and drive motor and power source requirements. Thus the cosmetic personalisation of a prosthesis to a particular patient can be substantially restricted to a non-structural outer cladding for the prosthesis. The form of construction used by the invention can moreover provide improved cosmeticisation opportunities as further discussed hereinbelow.

Another significant benefit of the present invention arises from the fact that a worm gear system is inherently substantially self-locking so that when the motor is switched off and stops driving a limb member which is still under load, the limb member is held in position and no additional mechanism is required in order to retain the limb member in a given position.

In general the drive motor means and any gearbox provided therewith, have a generally cylindrical form with an axially extending worm gear so that they can conveniently be mounted inside the end of an endoskeletal tube member with the drive output worm projecting axially outwardly therefrom. The power source could also be mounted inside the endoskeletal tube member but more conveniently could have a generally annular form (with a greater or lesser angular extent e.g. two units each having an angular extent of 180°) fitted around the outside of the endoskeletal tube member.

As noted above the prostheses of the invention may have one or more of a wrist joint, an elbow joint, and a shoulder joint, mechanically operable in accordance with the present invention. It would also be possible though to use, for example, an elbow joint according to the present invention in combination with a conventional mechanically operable wrist joint. Generally it will be more convenient to have the drive motor with its drive output worm mounted down-limb of the fixed worm gear wheel means. Thus in the case of a wrist joint the drive motor would preferably be inside the hand member and the fixed gear wheel means on the distal end of the forearm member. It would also be possible though for the drive motor to be inside the forearm member with the fixed worm gear wheel means mounted on the hand member. Similarly it would generally be preferred with an elbow joint for the drive motor to be in the forearm or lower arm member and the fixed worm gear wheels to be on the upper arm member; and with a shoulder joint, for the former to be in the upper arm member and the latter on a support body fitted in the shoulder of the patient. An advantage of the alternative arrangement of having the drive motor up-limb of the joint e.g. in the upper arm for an elbow joint, is that it raises the centre of gravity of the limb proximally thereby reducing the energy consumption and power requirements of the drive motor for that joint. It will of course be appreciated that, depending on the extent of the prosthesis, the support body for any given joint may comprise an endoskeletal tube member or some form of stump adaptor.

The endoskeletal tube members may have a variety of different forms and sizes depending, inter alia, on the materials used and the requirements of the individual patient. Thus the tube may be of polygonal e.g. square or hexagonal section, or could have a rounded, e.g.oval or elliptical section. Conveniently though there is used a generally plain cylindrical section as this is generally more easily available and more readily interfaceable with the other components of the prosthesis. The diameter may vary with strength and rigidity requirements which would generally increase from a hand member to a forearm member to an upper arm member. The tube wall thickness and material and construction will also affect the tube diameter. Advantageously the tubing is of woven and/or laminated carbon fibre which combines considerable strength with lightness. In this case the tubing could generally have a diameter in the range from 10 to 50 mm, preferably 12 to 40 mm with a wall thickness of from 0.5 mm to 5 mm, preferably from 1 to 2.5 mm. Thus for example in the case of a hand member there would typically be used tubing with a diameter of from 15 mm to 20 mm and in a lower or upper arm member tubing with a diameter of from 25 mm to 35 mm. Other materials could also be used though, e.g. high strength lightweight metal alloys such as duralumin™.

Various suitable motors having a relatively high power-to-weight ratio are known in the art including permanent magnet DC motors which have a substantially linear relation between torque and drive current over a reasonably wide range which facilitates control of the driving of the finger member. Particularly suitable motors are available from Minimotor SA of Switzerland, especially their motors which have a diameter of around 10 to 30 mm. A further advantage of this type of motor is the availability of a modular gearbox system coupled to the output shaft of the motor which allows different torque-output drive speed ratios to be selected simply by choosing from a range of gearboxes with different ratios. This has the advantage of facilitating the provision, in a multi-joint prosthesis, of different operating characteristics by simply using different gearboxes in different joints.

The use of cylindrical endoskeletal tube members also has the advantage of facilitating the incorporation of a rotational capability—especially in relation to wrist joints. This may be provided in generally known manner but the use of an endoskeletal form of construction has the additional advantage of allowing the use of cosmetic cladding which extends unbroken across the joint thereby avoiding the unsightly discontinuities that are present in conventional rotating wrist joints.

BRIEF DESCRIPTION OF THE DRAWINGS

Further preferred features and advantages of the invention will appear from the following detailed description given by way of example of some preferred embodiments illustrated with reference to the accompanying drawings in which.

DETAILED DESCRIPTION OF ILLUSTRATIVE EMBODIMENT

Figure 1:
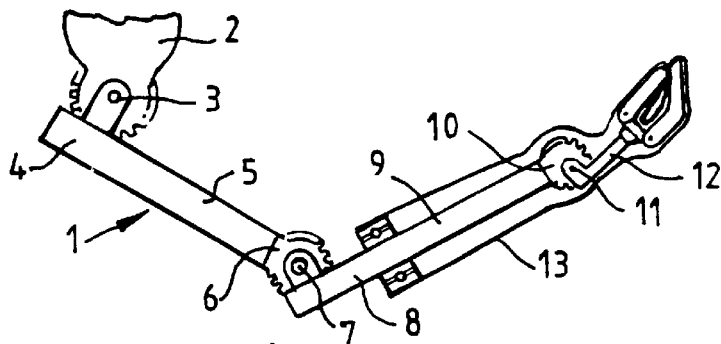
FIG. 1 is a schematic sectional view of a multi-joint prosthesis of the invention.

FIG. 1 shows an upper limb prosthesis 1 comprising a shoulder stump adaptor support body 2 pivotally connected 3 to the proximal, upper, end 4 of an upper arm member 5 whose distal, lower, end 6 is in turn pivotally connected 7 to the proximal, upper, end 8 of a forearm member 9 acting as a support body therefor. The distal, lower, end 10 of the latter is in turn pivotally connected 11 to a hand member 12. The forearm is covered in a flexible silicone rubber cosmetic cladding 13 prestretched over an arm bearing.

Figure 2:
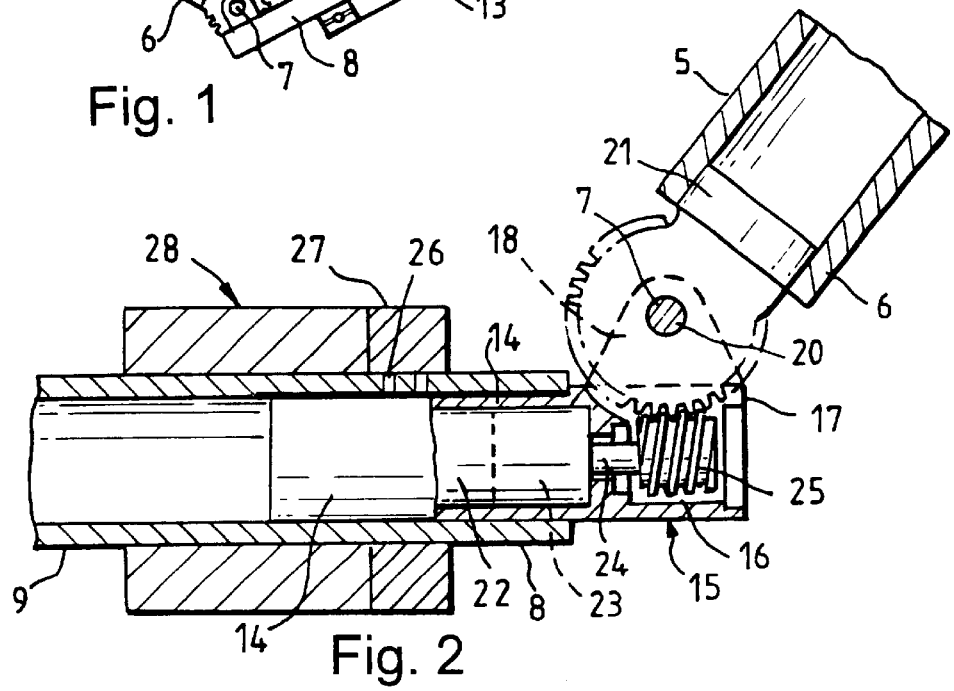
FIG. 2 is a detailed partly cut-away and sectioned view of the elbow joint of a prosthesis of the invention.

As shown in FIG. 2 into the upper end 8 of the forearm tube 9 is inserted a cylindrical housing end 14 of an adapter 15, the other end 16 of which has a pair of parallel opposed flanges 17 which project laterally 18 of the forearm tube 9. The projecting flange portions 18 receive therebetween a worm gear wheel 19 to which they are connected pivotally by a pivot pin 20. The worm gear wheel 19 has at one side a radially outwardly projecting cylindrical plug adapter 21 which is inserted and fixedly held (e.g. bonded, push-fit gripped, screwed in, clamped etc) inside the lower end 6 of the upper arm tube member 5 thereby fixedly holding the worm gear wheel.

Inside the cylindrical housing end 14 of the adapter 15 is mounted a drive motor 22 (which may be provided with an integral epicyclic gearbox 23) having a drive output shaft 24 on which is provided a worm gear 25 which extends between the flanges 17 for driving tangential inter-engagement with the worm gear wheel 19. The drive motor 22 is connected via electrical contact means 26 in the wall of the forearm tube 9, to the power supply control circuitry 27 of an annular battery pack 28 which fits closely around the tube 9. When the drive motor 22 is operated, the worm gear 25 draws itself and the forearm tube 9 around the fixed worm gear wheel 19 in a clockwise or anti-clockwise direction thereby swinging the forearm 9 up or down from the upper arm 5. In a particularly preferred form of embodiment the mounting of the fixed worm gear wheel 19 and the driven worm gear 25 with its drive motor, is reversed i.e. the former is mounted on the forearm 9 and the latter is mounted in the upper arm 5.

Figure 3:
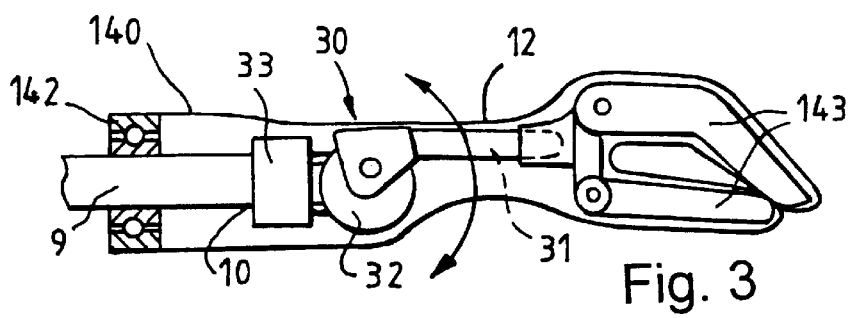
FIG. 3 is a detailed partly cut-away and sectioned view of the wrist joint of a prosthesis of the invention.
Figure 4:
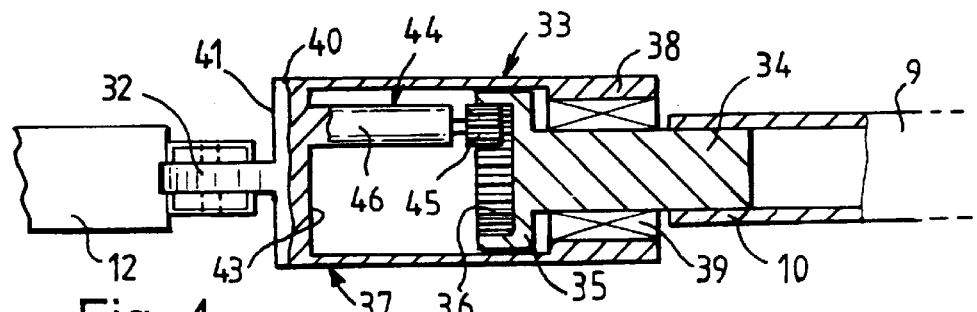
FIG. 4 is a detailed sectional view of the rotary actuator part of the wrist joint of FIG. 3.

FIG. 3 shows a wrist joint 30 which is of generally similar construction to that of the elbow joint of FIG. 2 albeit that in this case it will be appreciated that the hand tube 12 will be significantly shorter and may be somewhat smaller in diameter than the forearm tube 9 insofar as the strength requirements will be lower and a smaller motor 31 may be used. As described in more detail with reference to FIG. 4, the support body for the fixed worm gear wheel 32 on the lower end 10 of the forearm tube 9 is conveniently in the form of a rotary actuator connection 33 mounted on said lower end 10 of the tube 9.

In more detail the rotary connection 33 comprises a fixed stump portion 34 fixedly mounted in the distal end 10 of the forearm tube 9 and having at its distal end 35 a ring gear 36. A generally tubular wrist flexor support body 37 has an open end portion 38 rotatably mounted on the stump portion 34 via annular bearings 39 and a closed end portion 40 mounting on its outside face 41 the wrist flexor fixed worm gear wheel 32, and on its inside face 43 a spur pinion gear drive unit 44. The drive unit 44 extends parallel to but offset from the central longitudinal rotational axis of said support body 37 for driving engagement of the spur pinion gear 45 thereof with the ring gear 36 so that operation of the drive motor 46 of said drive unit 44 causes the wrist flexor support body 37 to rotate about said stump portion 34.

With this kind of arrangement the cosmetic hand cladding which is usually in the form of a suitably tinted silicone rubber glove 140 may be extended well up above the wrist joint itself where it can readily be concealed under a patient's clothing, the upper end 141 of the cladding 140 being simply supported via an annular bearing arrangement 142.

By using movable gripping fingers 143 in which the drive motors and gear means are mounted in the finger members themselves (as described in our earlier patent publication No WO95/24875)—rather than inside the body of the hand i.e. the palm portion of the prosthesis as with conventional prostheses—it is now for the first time possible to provide a prosthesis with wrist flexion together with wrist rotation and mechanically operable fingers.

What is claimed is:

1. An articular endoskeletal prosthesis for providing a user with a mechanically operable pivoting and rotating wrist joint, said prosthesis having at least one elongate forearm endoskeletal tube upper limb member with a proximal end portion having a pivotal connection to a support body therefor, one of said upper limb member proximal end portion and said support body having a fixed worm gear wheel provided with gear teeth and the other a drive motor having a drive output worm extending generally tangentially of said fixed worm gear wheel in captive engagement with said gear teeth of said fixed worm gear wheel so that when said drive motor is operated, in use of the prosthesis, said drive output worm moves around said fixed worm gear wheel so as to pivot said upper limb member about its pivotal connection relative to said support body wherein said wrist joint is provided, at its up-joint side with a rotary actuator connection which comprises a fixed stump portion fixedly mounted in the distal end of a forearm endoskeletal tube, and having at said distal end a ring gear, a tubular wrist flexor support body having an open end portion rotatably mounted on said stump portion via annular bearings, and a closed end portion mounting, on its outside face, the wrist flexor fixed worm gear wheel, and on its inside face a spur pinion gear drive unit, wherein said drive unit extends parallel to, but offset from the central longitudinal rotational axis of said wrist flexor support body for driving engagement of the spur pinion gear thereof with said ring gear so that operation of the drive motor of said drive unit causes, in use of the prosthesis, the wrist flexor support body to rotate about said stump portion.

2. An articular endoskeletal prosthesis according to claim 1 for further providing a user with at least one of a mechanically operable pivoting, elbow and shoulder joint, having at least one elongate endoskeletal tube upper limb member with a proximal end portion having a pivotal connection to a support body therefor, one of said upper limb member proximal end portion and said support body having a fixed worm gear wheel provided with gear teeth and the other a drive motor having a drive output worm extending generally tangentially of said fixed worm gear wheel in captive engagement with said gear teeth of said fixed worm gear wheel so that when said drive motor is operated, in use of the prosthesis, said drive output worm moves around said fixed worm gear wheel so as to pivot said upper limb member about its pivotal connection relative to said support body.

3. An articular endoskeletal prosthesis according to claim 2, wherein a said endoskeletal tube member of said wrist joint has a diameter which is less than that of a said endoskeletal tube member of a said elbow or shoulder joint.

4. An articular endoskeletal prosthesis according to claim 1 wherein said prosthesis includes a said wrist joint, a said elbow joint, and a said shoulder joint, wherein said shoulder joint has a shoulder adaptor support body pivotally connected to an upper arm endoskeletal tube member, said upper arm tube member having a distal end portion constituting a support body for said elbow joint, said elbow joint support body being pivotally connected to a said forearm endoskeletal tube member.

5. An articular endoskeletal prosthesis according to claim 1, wherein the drive motor is provided with a gearbox, said drive motor and gearbox having a generally cylindrical form with an axially extending worm gear so as to facilitate mounting thereof inside the end of an endoskeletal tube member with the drive output worm projecting axially outwardly therefrom.

6. An articular endoskeletal prosthesis according to claim 1, wherein the drive motor with its drive output worm is mounted on said upper limb member and the fixed worm gear wheel is mounted on said support body.

7. An articular endoskeletal prosthesis according to claim 1, wherein the drive motor is mounted on said support body and the fixed worm gear wheel is mounted on said upper limb member.

8. An articular endoskeletal prosthesis according to claim 1, wherein said support body comprises an endoskeletal tube member or a stump adaptor.

9. An articular endoskeletal prosthesis according to claim 1 wherein said endoskeletal tube member is formed from woven and/or laminated carbon fibre or a high strength lightweight metal alloy.

10. An articular endoskeletal prosthesis according to claim 1, wherein said drive motor is a permanent magnet D.C. motor having a substantially linear relation between torque and drive current.

11. An articular endoskeletal prosthesis according to claim 1, wherein said drive motor has an output shaft, and further has coupled in-line with said output shaft a gear box, wherein said gear box is chosen from a range of gear boxes wherein said range of gear boxes provides a variety of gearing ratios such that different torque-output drive speeds are selected by choosing the appropriate gear box with the desired gearing ratios from the range.

12. An articular endoskeletal prosthesis according to claim 1, wherein there is provided a cosmetic cladding which extends unbroken across a said at least one joint in use of said prosthesis.

13. An articular endoskeletal prosthesis according to claim 1, wherein, in use of the prosthesis, there is provided a power source for said motor.

14. An articular endoskeletal prosthesis according claim 13, wherein said power source is of a generally annular or part-annular form for mounting on the outside of a said endoskeletal tube member.

15. An articular endoskeletal prosthesis according to claim 1 which includes a cosmetic hand cladding which extends unbroken up above said wrist joint, the upper end of said hand cladding being mounted on an annular bearing mounted on said forearm endoskeletal tube.

16. An articular endoskeletal prosthesis according to claim 1 wherein said fixed worm gear wheel is arranged concentrically with said pivotal connection.

* * * * *